United States Patent
Murugesan

(10) Patent No.: US 12,009,059 B2
(45) Date of Patent: Jun. 11, 2024

(54) ANALYTIC PREDICTION OF ANTIBIOTIC SUSCEPTIBILITY

(71) Applicant: KONINKLIJKE PHILIPS N.V., Eindhoven (NL)

(72) Inventor: Karthikeyan Murugesan, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1337 days.

(21) Appl. No.: 16/463,710

(22) PCT Filed: Nov. 27, 2017

(86) PCT No.: PCT/EP2017/080550
§ 371 (c)(1),
(2) Date: May 23, 2019

(87) PCT Pub. No.: WO2018/096153
PCT Pub. Date: May 31, 2018

(65) Prior Publication Data
US 2019/0279738 A1    Sep. 12, 2019

Related U.S. Application Data

(60) Provisional application No. 62/511,051, filed on May 25, 2017, provisional application No. 62/426,775, filed on Nov. 28, 2016.

(51) Int. Cl.
*G06N 20/00*    (2019.01)
*G16B 20/00*    (2019.01)
(Continued)

(52) U.S. Cl.
CPC ............. *G16B 20/00* (2019.02); *G06N 20/00* (2019.01); *G16B 40/00* (2019.02); *G16B 50/20* (2019.02)

(58) Field of Classification Search
None
See application file for complete search history.

(56) References Cited

U.S. PATENT DOCUMENTS

2003/0190603 A1    10/2003    Larder
2004/0022430 A1    2/2004     Franssen
(Continued)

FOREIGN PATENT DOCUMENTS

CN    105136454 A       12/2015
WO    WO-2017075294 A1 *  5/2017    ......... C12N 15/1075

OTHER PUBLICATIONS

Walker, Timothy M. et al., "Whole-genome sequencing for prediction of *Mycobacterum tuberculosis* drug susceptibility and resistance: a retrospective cohort study", The Lancet Infectious Diseases, vol. 15, No. 10, (Jun. 24, 2015), pp. 1193-1202.
(Continued)

*Primary Examiner* — David R Vincent

(57) ABSTRACT

Methods and systems for predicting the susceptibility of bacterial pathogens to antibiotics using genomic data sets. Various embodiments described herein receive a genomic dataset and a set of labels and run principal variance component analysis thereon to determine the effect sizes of the labels. One or more labels are then selected based on their effect sizes and used in a machine learning model to make predictions on future datasets.

14 Claims, 4 Drawing Sheets

(51) Int. Cl.
  *G16B 40/00* (2019.01)
  *G16B 50/20* (2019.01)

(56) References Cited

U.S. PATENT DOCUMENTS

| | | | |
|---|---|---|---|
| 2006/0064415 A1* | 3/2006 | Guyon | G16B 40/10 |
| 2013/0304783 A1 | 11/2013 | Fontes | |
| 2015/0186596 A1 | 7/2015 | Chakrabarti et al. | |
| 2016/0016263 A1 | 1/2016 | Burbaum | |
| 2016/0117441 A1 | 4/2016 | Bremel | |
| 2016/0138105 A1* | 5/2016 | McCoy | G16B 30/00 |
| | | | 702/19 |
| 2019/0355440 A1 | 11/2019 | Ranjeet | |

OTHER PUBLICATIONS

Niehaus, et al., "Machine Learning for the prediction of antibacterial susceptibility in *Mycobacterium tuberculosis*", IEEE-EMBS International Conference on Biomedical and Health Informatics, Jun. 1, 2014, pp. 618-621.

Coelho, et al., "The Use of Machine Learning Methodologies to Analyse Antibiotic and Biocide Susceptibility in *Staphylococcus aureus*", PLOS ONE, Feb. 19, 2013, vol. 8, No. 2, p. e55582, 10 pages.

Yang, et al., "Predicting antibiotic resistance from genomic data" In: "Machine Learning for Healthcare Technologies", Oct. 28, 2016, Institution of Engineering and Technology, pp. 203-226.

International Search and Written Opinion for International Application No. PCT/EP2017/080550, filed Nov. 27, 2017, 15 pages.

Lazar, et al., "Batch effect removal methods for microarray gene expression data integration: a survey", Briefings in Bioinformatics, Published Jul. 31, 2012, vol. 14, No. 4, pp. 469-490.

Hornung, et al., "Combining location-and-scale batch effect adjustment with data cleaning by latent factor adjustment", Sep. 22, 2015, Technical Report No. 184,2015, Department of Statistics, University of Munich, pp. 1-35.

Brezina, et al., "Immune Signatures for Lung Cancer Diagnostics: Evaluation of Protein Microarray Data Normalization Strategies", Microarrays 2015, 4, pp. 162-187.

Leavey, et al., "Large Scale Aggregate Microarray Analysis Reveals Three Distinct Molecular Subclasses of Human Preeclampsia", PLOS One, Feb. 13, 2015, pp. 1-21.

Scherer, A., "Batch Effects and Noice in Microarray Experiments: Sources and Solutions", The Wiley Network, Dec. 2009, 4 pages (Abstract).

Bushel, P., "Principal Variance Component Analysis (PVCA)", Bioconductor—PVCA, 4 pages. (Abstract).

Breiman, et al., "Random Forest Package From R", "Breiman and Cutler's Random Forests for Classification and Regression", Mar. 25, 2018, pp. 1-29. (Abstract).

McArthur, et al. "The Comprehensive Antibiotic Resistance Database", Antimicrobial Agents and Chemotherapy, vol. 57, No. 7, Jul. 2013, pp. 3348-3357.

Zankari, et al., "Identification of acquired antimicrobial resistance genes", Journal of Antimicrobial Chemotherapy 2012, 67, pp. 2640-2644.

\* cited by examiner

ANALYTIC PREDICTION OF ANTIBIOTIC SUSCEPTIBILITY

RELATED APPLICATIONS

This application is the U.S. National Phase application under 35 U.S.C. § 371 of International Application No. PCT/EP2017/080550, filed on Nov. 27, 2017, which claims the benefit of both Provisional Application Ser. No. 62/511,051, filed May 25, 2017 and Provisional Application Ser. No. 62/426,775, filed Nov. 28, 2016. These applications are hereby incorporated by reference herein, for all purposes.

TECHNICAL FIELD

Embodiments described herein generally relate to systems and methods for predicting antibiotic drug susceptibility of bacterial pathogens from genomic datasets and, more particularly but not exclusively, to systems and methods for predicting antibiotic drug susceptibility of bacterial pathogens from genomic datasets using principle variance component analysis reinforced machine learning.

BACKGROUND

Machine learning techniques have become widely used as powerful tools to analyze and process complex data sets. Blindly applying machine learning techniques to these large and often incompatible datasets at times leads to overkill analytics, false interpretations, and the overfitting of data.

Specifically, the structure of these datasets often includes a matrix of features and a matrix or single vector of labels. In the realm of genomic datasets, the matrix of features may include isolates and genes, for example. Technically, a multi-label classifier can be built to learn the nuances of feature-label associations across all features and labels in the matrices to map a new input observation to a vector of labels. Oftentimes, however, the labels used are not significant for classifying features or can lead to inaccurate classifications.

A need exists, therefore, for methods and systems that assess the ability of labels from a dataset to accurately predict features for drug susceptibility even before building a machine learning model.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments relate to a method of training a model for predicting antibiotic drug susceptibility. The method includes receiving, via an interface, a data set of a plurality of features; receiving, via the interface, a set of labels that are related to the plurality of features; supplying the data set of the plurality of features and the set of labels to a processor configured to execute instructions stored on a memory to provide a variance analysis engine, wherein the variance analysis engine is configured to generate an effect size for each of the labels on the data set of the plurality of features; supplying as output from the variance analysis engine to a sizing module at least one effect size generated for a label; and selecting, via the sizing module, at least one label to be used in a machine learning model based on the at least one supplied effect size.

In some embodiments, the data set of the plurality of features is a genomic dataset including at least one of a gene presence-absence matrix, an SNP matrix, a plasmid profiling matrix, a mobile genetic element matrix, a gene expression matrix, an RNA sequence matrix, and a microarray matrix.

In some embodiments, the set of labels is a covariate matrix including a plurality of phenotypes. In some embodiments, the set of labels is a single vector of binary values. In some embodiments, the set of labels is a single vector of multi-class values.

In some embodiments, selecting the at least one label via the sizing module includes selecting the at least one label based on its generated effect size exceeding a predetermined threshold.

In some embodiments, the method further includes ranking, via the sizing module, the plurality of labels based on their effect size and selecting, via the sizing module, the at least one label based on the ranking.

According to another aspect, embodiments relate to a system for training a model for predicting antibiotic drug susceptibility. The system includes an interface for receiving a data set of a plurality of features and a set of labels that are related to the plurality of features; a memory; and a processor configured to execute instructions stored on the memory to provide a variance analysis engine configured to receive the data set of the plurality of features and the set of labels and further configured to output an effect size for each of the labels, wherein at least one label is selected to be used in a machine learning model based on its effect size.

In some embodiments, the data set of the plurality of features is a genomic dataset including at least one of a gene presence-absence matrix, an SNP matrix, a plasmid profiling matrix, a mobile genetic element matrix, a gene expression matrix, an RNA sequence matrix, and a microarray matrix.

In some embodiments, the set of labels is a covariate matrix including a plurality of phenotypes. In some embodiments, the set of labels is a single vector of binary values. In some embodiments, the set of labels is a single vector of multi-class values.

In some embodiments, the at least one selected label is selected based on its generated effect size exceeding a predetermined threshold.

In some embodiments, the variance analysis engine is further configured to rank the set of labels based on their effect size and select the at least one label based on the ranking.

According to yet another aspect, embodiments relate to a method for training an antibiotic resistance model. The method includes receiving, via an interface, a feature matrix including a plurality of genomic features and a plurality of isolates; receiving, via the interface, a covariate matrix including a plurality of phenotypes and the plurality of isolates; inputting the feature matrix and the covariate matrix into a processor executing instructions stored on a memory to provide a variance analysis engine; supplying an effect size of each of the plurality of phenotypes from the variance analysis engine to a sizing module; and selecting, via the sizing module, at least one of the phenotypes to train an antibiotic resistance machine learning model based on the effect size of the at least one selected phenotype.

BRIEF DESCRIPTION OF DRAWINGS

Non-limiting and non-exhaustive embodiments of the invention are described with reference to the following

DETAILED DESCRIPTION

Figure 1:
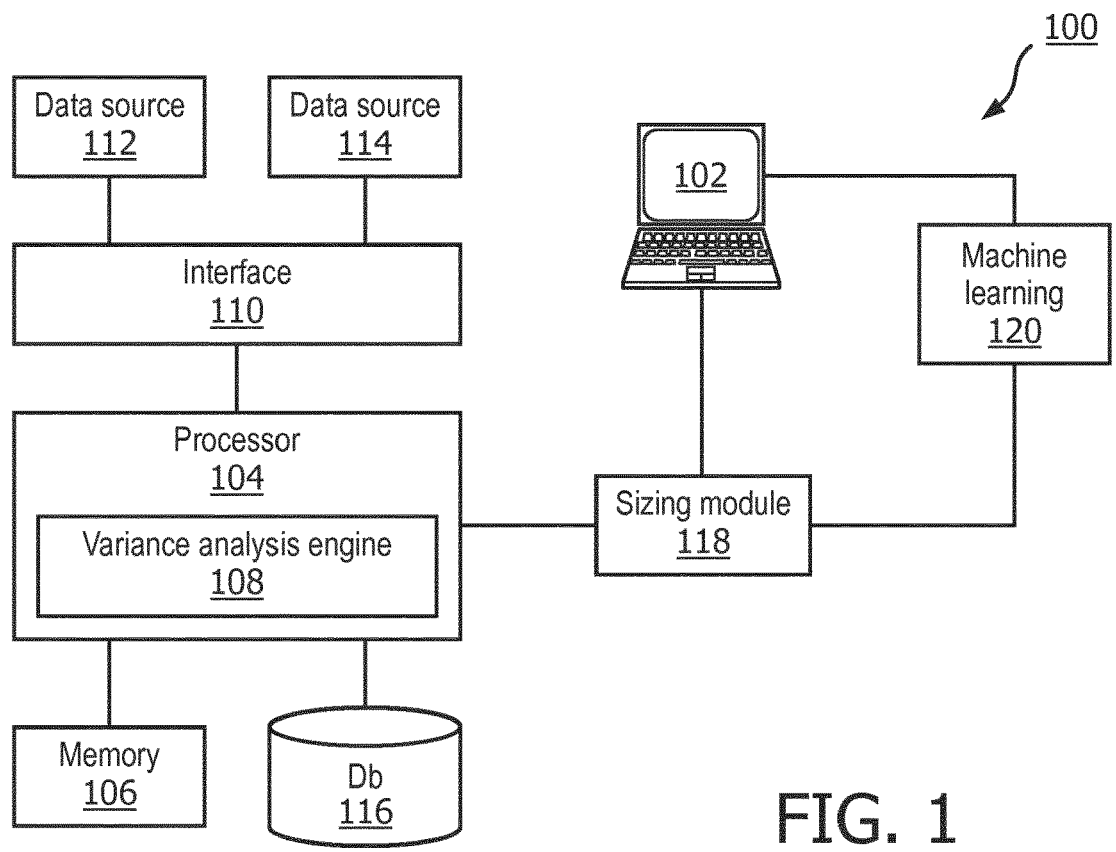
FIG. 1 illustrates a system for training a model in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

As mentioned previously, there is a need to assess the antibiotic drug susceptibility of bacterial pathogens from genomic datasets. In the course of doing so, it is sometimes necessary to assess the ability of labels to accurately predict features before building a machine learning-based model to predict drug susceptibility.

Oftentimes there is no significant pattern of association between labels and observations. That is, a particular label does not necessarily relate to an observation or observations in a statistically meaningful sense. Accordingly, including these types of labels in a model would unnecessarily consume processing power and perhaps lead to inaccurate classifications. Accordingly, choosing labels that can be predicted accurately may simplify and improve the model.

Various embodiments of the methods and systems described herein therefore select certain labels for use in constructing a machine learning model suitable for predicting pathogen vulnerability to various antibiotics. This machine learning model may be a random forest model, for example.

A method in accordance with one embodiment may begin by first accessing or otherwise receiving a matrix of, e.g., genomic features and a matrix or vector of labels. The method may then apply a principal variance component analysis (hereinafter "PVCA") to the dataset to obtain the effect sizes or variance contribution of each potential label in the dataset. Labels with a high variance contribution or effect sizes may be selected or presented to a user for selection. These potential labels may be used as labels in training a machine learning model for future datasets.

PVCA may rank the effect sizes of the labels on the dataset. From this analysis, one can estimate what labels are suitable to be predicted using the dataset. The lower the effect size of the covariate, the lower the accuracy of the prediction (i.e., there will be a higher error rate) generally speaking. Select labels, e.g., labels with high effect sizes, may then be used as a predictor/label in a machine learning model such as a random forest model.

Historically, PVCA was a technique built on principal component analysis (PCA) and variance component analysis (VCA). This technique was used to estimate the variability of various experimental effects on gene expression data. In addition to biological and genetic effects, these experimental effects may include other types of environmental, population, technical, and confounding factors that could potentially have an effect on gene expression values.

PVCA helps estimate the variance in a genomic dataset that is due to each of the given covariates, and attributes the remaining variance to residual effects. In other words, it combines PCA and VCA to reduce the feature space into a fewer number of dimensions. PVCA may then fit a mixed linear model using factors of interest as random effects to estimate and partition the total variability.

The functionality that PVCA provides in estimating the variance proportion of each covariate is not limited to gene expression datasets. Rather, PVCA can also estimate label importance to choose labels that are worth predicting in other types of multi-label classification datasets.

FIG. 1 illustrates a system 100 for training a model in accordance with one embodiment. In some embodiments, the model may be used to predict antibiotic drug susceptibility of bacterial pathogens from genomic datasets. The system 100 may include a user input/output (I/O) device 102 and a processor 104 executing instructions stored on memory 106 to provide a variance analysis engine 108. The processor 104 may be in communication with or otherwise include an interface 110 receiving data from one or more gene data sources 112 and 114. The system 100 may also include one or more databases 116 in communication with the processor 104.

The output of the processor 104 and, namely, the variance analysis engine 108 may include effect sizes for one or more covariates. The effect sizes may be communicated to a sizing module 118.

The sizing module 118 may rank or otherwise sort the various covariates based on their effect size. The sizing module 118 may also output a list of the covariates and their effect sizes. For example, the sizing module 118 may output the covariates with the three highest effect sizes. An operator may view these covariates via the I/O device 102. Additionally, certain covariates may be selected automatically or by the operator for use in a machine learning module 120.

The I/O device 102 may be any suitable device that can receive commands from an operator and output data regarding genomic data, phenotypes, covariates, and their associated effect sizes. The I/O device 102 may be configured as, for example but without limitation, a personal computer, a tablet, laptop, mobile device, a smartwatch, or the like.

The processor 104 may be any specifically configured processor or hardware device capable of executing instructions stored on memory 106 to at least provide a variance analysis engine 108. The processor 104 may include a microprocessor, a field programmable gate array (FPGA), application-specific integrated circuit (ASIC), or other similar device. In some embodiments, such as those relying on one or more ASICs, the functionality described as being provided in part via software may instead be hardwired into the operation of the ASICs, and as such, any associated software may be omitted.

The memory 106 may be L1, L2, L3 cache or RAM memory configurations. The memory 106 may include non-volatile memory such as flash memory, EPROM, EEPROM, ROM, and PROM, or volatile memory such as static or dynamic RAM, as discussed above. The exact configuration/type of memory 106 may of course vary as long as instructions for analyzing genomic data and instructions for generating effect sizes for covariates can be executed by the processor 104.

The variance analysis engine 108 may be configured to calculate the effect sizes or variance contribution of various covariates. In the clinical realm, these covariates may include but are not limited to age, year, isolate collection date, isolate sequencing date, and susceptibilities to various antibiotics (e.g., Penicillin, Vancomycin, Tetracycline, etc.).

The interface 110 may receive gene expression data from one or more data sources 112 and 114. The interface 110 may then communicate the received data to the processor 104 for analysis. The received gene expression data may include, but is not limited to, a data set of a plurality of features and a data set of a plurality of labels related to the features.

The database(s) 116 may store data regarding effect sizes of certain covariates. For example, the database(s) 116 may store data regarding results of previous PVCA processes executed on certain datasets.

After analysis of the received data, the variance analysis engine 108 may output data regarding covariates and their effect sizes to the sizing module 118. The sizing module 118 may be any specifically configured processor or hardware device capable of sizing, ranking, or otherwise sorting covariates based on their effect sizes. The sizing module 118 may include a microprocessor, a field programmable gate array (FPGA), application-specific integrated circuit (ASIC), or other similar device. In some embodiments, such as those relying on one or more ASICs, the functionality described as being provided in part via software may instead be hardwired into the operation of the ASICs, and as such, any associated software may be omitted.

From this analysis, the system 100 can estimate what labels are suitable to be predicted using the dataset. These labels may then be used to build an accurate learning model. Accordingly, the sizing module 118 may output a list of covariates with the highest effect sizes to the I/O device 102 for presentation to an operator. The selected covariates may then be used in a machine learning model 120.

Figure 2:
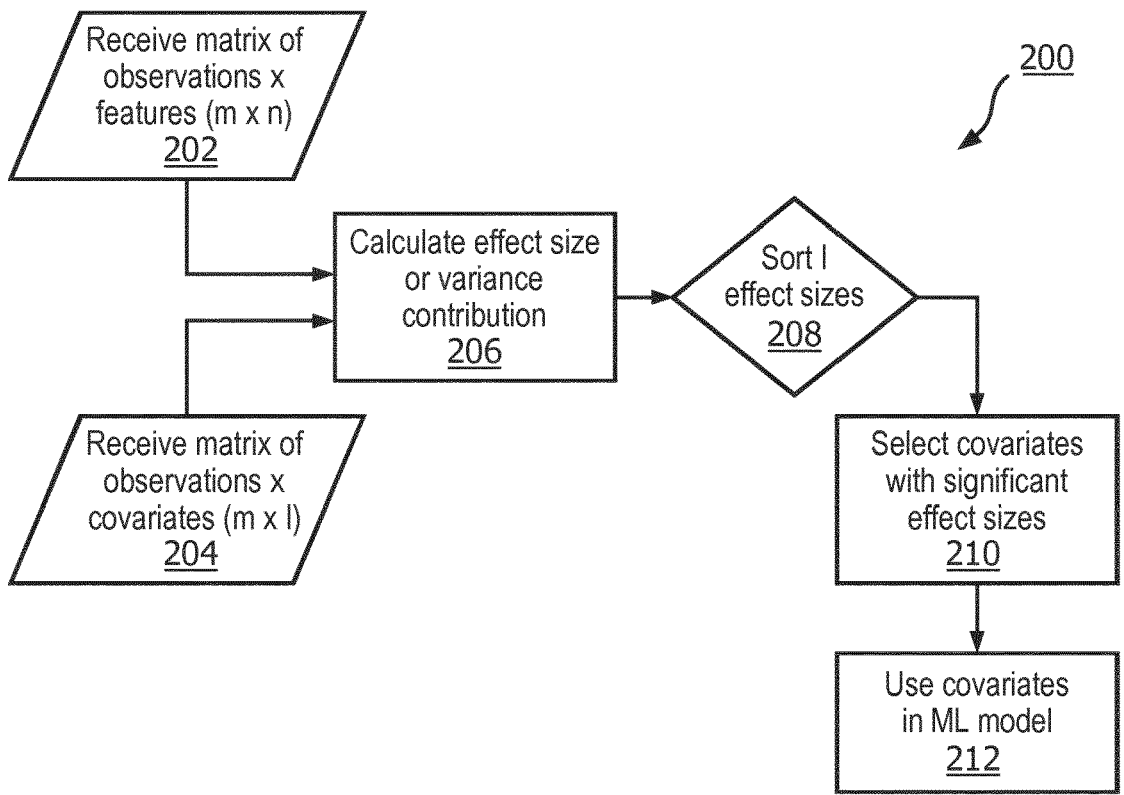
FIG. 2 depicts a flowchart of a method for training a model using the system of FIG. 1 in accordance with one embodiment.

FIG. 2 depicts a flowchart of a method 200 of training a model using the system of FIG. 1 in accordance with one embodiment. Step 202 involves receiving a matrix of Observations×Features (m×n). A processor such as the processor 104 of FIG. 1 may receive this matrix from a data source such as the data source 112 of FIG. 1.

In embodiments relating to antibiotic resistance prediction, this matrix m×n may be a matrix of genes and isolates. Or, in other embodiments, matrix m×n may be a matrix of antibiotic resistance genes and isolates. This genomic data set may also be at least one of a gene presence-absence matrix, a single nucleotide polymorphism (SNP) matrix, a plasmid profiling matrix, or the like.

Step 204 involves receiving a matrix of observations and covariates/labels (m×l). The processor 104 of FIG. 1 may receive this data from a data source such as the data source 114 of FIG. 1.

Oftentimes there are many labels that can be associated with observations and can be binary or multi-class labels. In some embodiments, the labels may be a single vector of labels (m×1), which can be binary or multi-class. In embodiments relating to antibiotic resistance prediction, the matrix m×l may be a covariate matrix including isolates and phenotype labels.

Step 206 involves analyzing the matrices m×n and m×l to calculate the effect size of the various covariates. This step 206 may be performed by a variance analysis engine such as the variance analysis engine 108 of FIG. 1. In this embodiment the variance analysis engine 108 may have received a data matrix of isolates and phenotype labels (m×l) designated as Covariate.Matrix, a data matrix of all genes and isolates designated as All.genes, and a data matrix of antibiotic resistance genes and isolates designated as abRes.Genes. The variance analysis engine 108 may then execute the below pseudocode to analyze the received matrices:

```
covariate.PhenoData <- new("AnnotatedDataFrame", data = Covariate.Matrix).
This creates an object of type AnnotatedDataFrame (Biobase data structure) to store the
phenotype/covariate data of the isolates.
All.expressionSet <- new("ExpressionSet", exprs = All.genes,
phenoData = covariate.phenoData)
abRes.expressionSet <- new("ExpressionSet", exprs = abRes.Genes,
phenoData = covariate.phenoData).
Creates ExpressionSet objects (Biobase data structure) to store the isolate gene presence
absence datasets
pct_threshold <- 0.6.
##PVCA Threshold Value is the percentile value of the minimum amount of the variabilities that
the selected principal components need to explain (value between 0 and 1).
batch.factors<-c("MLST",      "DAP.Int",      "AM.Int.",
"Lzd.Int", "P.int", "Rif.Int", "Syn.Int", "Te.Int", "Year", "Age
.Cat").
##These are the covariates used to partition the variability in the dataset of features.
abRes.pvcaObj<-pvcaBatchAssess(abRes.expressionSet, batch.factors,
pct_threshold) All.pvcaObj <- pvcaBatchAssess(All.expressionSet,
batch.factors, pct_threshold).
##Principal Variance Component Analysis.
```

The pvcaBatchAssess function returns the effect sizes of the covariates on the dataset. In this embodiment, these covariates include age (Age.Cat), year (Year), susceptibility to Amikacin (AM.Int), susceptibility to Daptomycin (DAP.Int), susceptibility to Linezolid (Lzd.Int), susceptibility to Penicillin (P.Int), susceptibility to Rifampcin (Rif.Int), susceptibility to Tetracycline (Te.Int) and variations in a sequence measured by multilocous sequence typing (MLST).

Scripts can be developed to implement the PVCA. However, a well-documented, popular PVCA module is available as an R package provided by Bioconductor at haps://www.bioconductor.org/packages/release/bioc/htmlipvca.html.

Referring back to FIG. 2, step 208 involves sorting the effect sizes of the labels 1. This step may be performed by a sizing module such as the sizing module 118 of FIG. 1. The sizing module 118 may, for example, output a list of the labels according to their effect sizes in ascending or descending order. Or, the sizing module 118 may group labels into groups according to percentiles.

Step 210 involves selecting covariates (i.e., the labels) based on their effect sizes. This step may be performed by the sizing module 118 of FIG. 1. In some embodiments, for example, the sizing module 118 may be configured to select the labels with the three highest effect sizes. Or, in other embodiments, the sizing module 118 may select all labels with an effect size that exceeds a predetermined threshold. In yet other embodiments, the sizing module 118 may output a list of all labels to a user interface such as the I/O device 102 of FIG. 1. An operator may then view the list and select the covariates himself.

Step 212 involves using the selected covariates in a machine learning model. This may be a random forest model, for example, and may be used to make predictions on future datasets. Step 212 may be executed by the below pseudocode:

```
rf<- randomForest(x = t(gene presence absence dataset) , y =
as.factor(label), importance = TRUE, ntree 10000, proximity =
TRUE).
return(summary(rf$err.rate)).
Selected Covariates may then be used in a Random Forest module.
```

A random forest model can be built using the randomForest package from the Comprehensive R Archive Network (CRAN). This package is available at https://cran.r-project.org/web/packages/randomForest/randomForest.pdf.

The method 200 of FIG. 2 was run on a covariate matrix, a genes matrix (referred to below as "All.Genes") and an antibiotic resistance matrix of antibiotic resistance genes x isolates (referred to below as "abRes.Genes").

The covariate matrix included 308 isolates×10 phenotypes labels. The phenotype labels (i.e., the covariates) included those discussed above.

The All.Genes matrix included 6094 genes×308 isolates. These 6094 high variance genes were filtered from a total gene set of approximately 13,000 genes that were predicted from 308 E. faecium genomes.

The abRes.Genes matrix included 180 genes×308 isolates. The 180 genes were received from a combined repository of CARD and Resfinder and included those that were present in at least one of the 308 E. faecium isolates.

Figure 3:
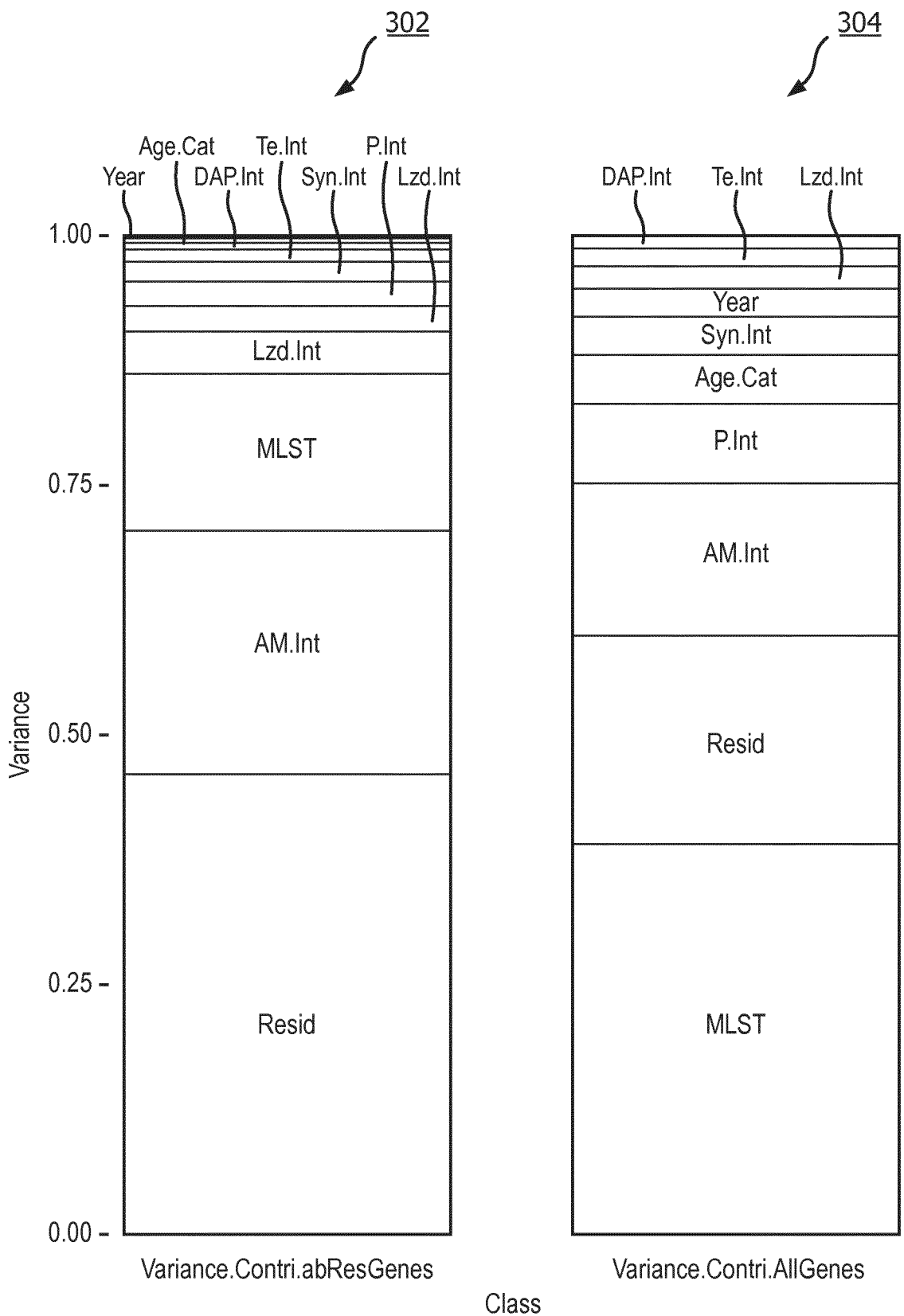
FIG. 3 depicts bar graphs showing the variance of several covariates on an antibiotic resistance matrix and a gene matrix in accordance in accordance with one embodiment.

PVCA is run on this data set to compute the effect sizes of the various covariates on the two genomic datasets. FIG. 3 depicts two stacked bar graphs 302 and 304 showing the variance (i.e., effect size) of the covariates from the abRes.Genes matrix and the All.Genes matrix, respectively.

As can be seen in graph 302, for example, residual effects have a variance of approximately 0.45 for the abRes.Genes matrix 302. It is noted that residual effects are generally neglected and are not considered when creating a machine learning model.

According to graph 302, the covariate with the next highest variance for the abRes.Genes matrix is susceptibility to Amikacin (Am.Int) with a variance of approximately 0.25. Covariates such as Year and Age, on the other hand, have extremely small effect sizes. It is noted that the sum of the variance values each class is 1.00.

The sizing module 118 may output stacked bar graphs such as the graphs 302 and 304 to the I/O device 102 for presentation to an operator. The sizing module 118 and the I/O device 102 may be configured to present only select covariates depending on the preferences of the user. For example, the sizing module 118 may be configured to output only the covariates with the three highest effect sizes. The I/O device 102 may include or otherwise be configured with one or more graphical processing units (GPUs) to present the covariates and their effect sizes in a number of formats such as a bar graph, list, table, or the like.

The sizing module 118 and/or an operator may select certain covariates to be used in a machine learning model based on their effect sizes. This machine learning model may be, e.g., a random forest model used to predict labels from additional feature sets.

Figure 4:
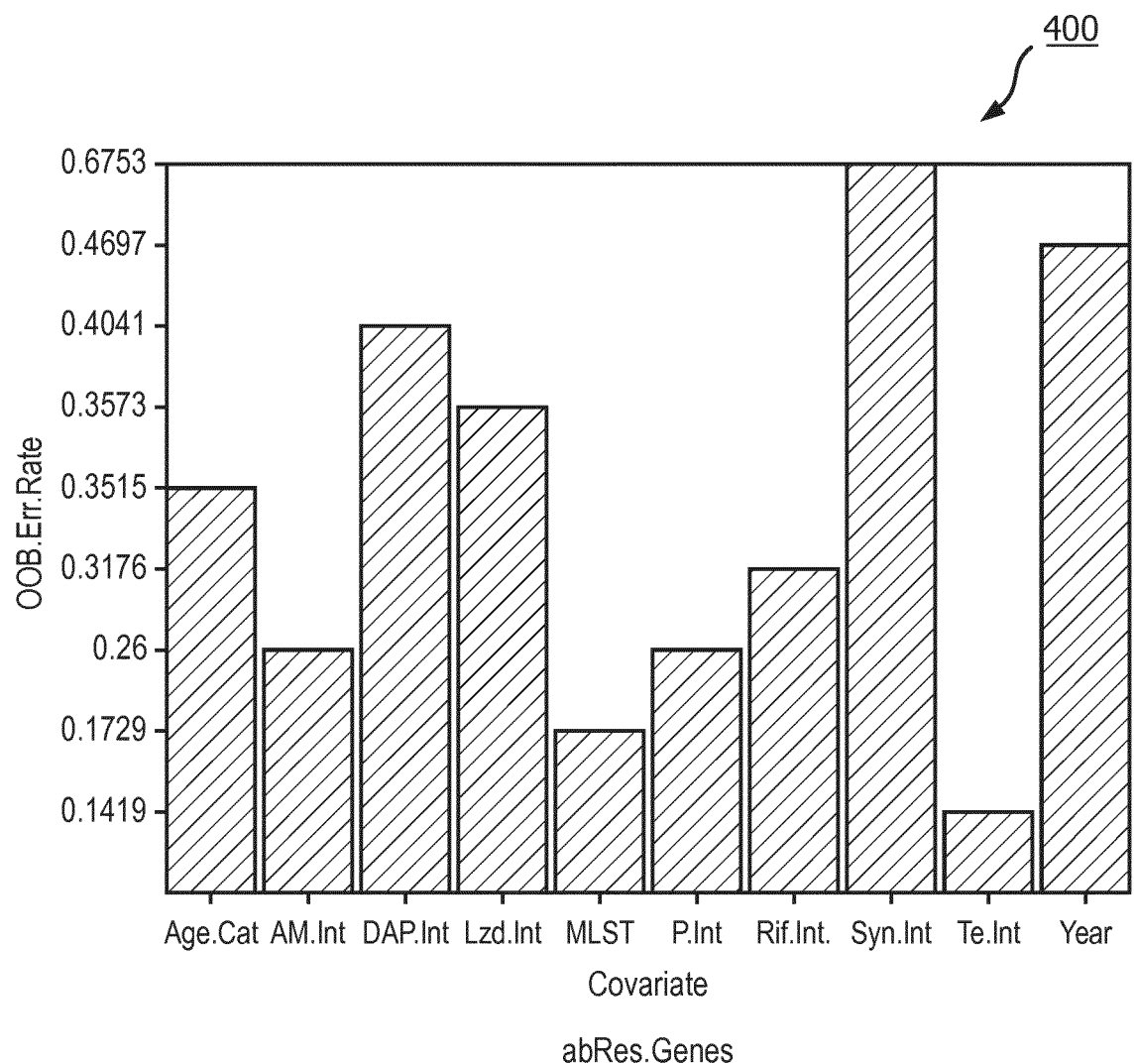
FIG. 4 depicts a bar graph of error rates of covariates on the antibiotic gene resistance feature set of FIG. 3 in accordance with one embodiment.

FIG. 4 illustrates a bar graph 400 showing the out-of-bag (OOB) error rates for each of the covariates when a random forest model is built on the abRes.Genes matrix. As can be seen, the OOB error rate for MLST is quite low. This makes sense as the effect size of MLST on the abRes.Genes dataset has a relatively significant value of approximately 18%, as seen in graph 302 of FIG. 3.

Graph 400 also shows that covariates such as Age and Year have relatively large OOB error rates. This makes sense as they both had relatively insignificant effect sizes.

Figure 5:
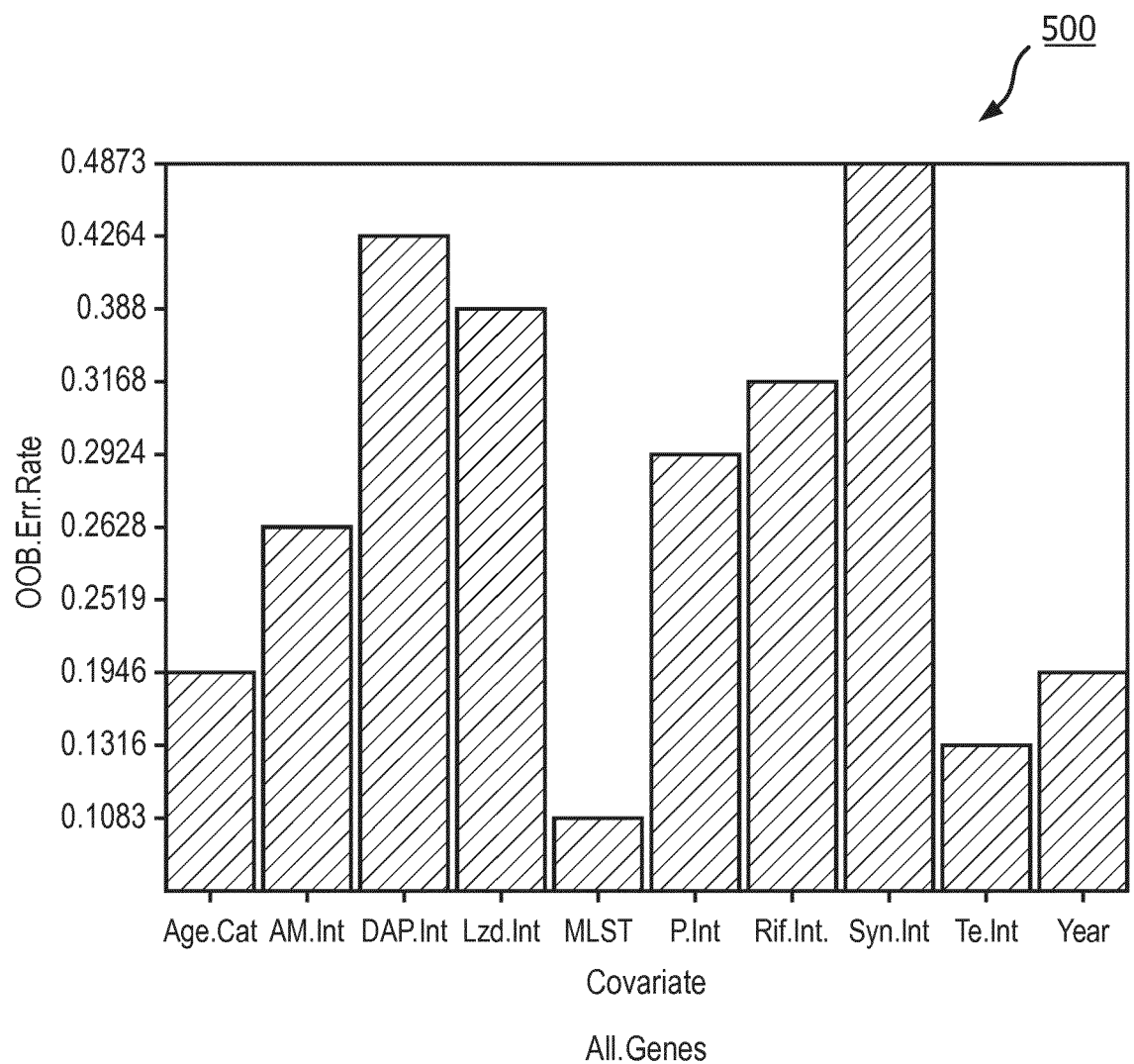
FIG. 5 depicts a bar graph of error rates of covariates on the gene feature set of FIG. 3 in accordance with one embodiment.

FIG. 5 illustrates a bar graph 500 showing the OOB error rates for each of the covariates when a random forest model is built on the All.Genes matrix. Graph 500 shows that the OOB error rate for MLST for this model is also quite low with a value of approximately 0.1083. Again, this makes sense as the effect size of MLST on the All.Genes dataset has a relatively high value of approximately 40% as seen in the graph 304 of FIG. 3.

Features of various embodiments described herein can be implemented across multiple domains in which machine learning is used. These applications may range from bioinformatics to online advertising, speech recognition, handwriting recognition, marketing, recommendation systems, and others. Accordingly, features of various embodiments described herein can be help users make educated judgments on what can be predicted using a dataset of features.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A method of training a model for predicting antibiotic drug susceptibility, the method comprising:
    receiving, via an interface, a data set of a plurality of features;
    receiving, via the interface, a set of labels that are related to the plurality of features, wherein the set of labels is a covariate matrix including a plurality of phenotypes, and the plurality of phenotypes includes susceptibilities to various antibiotics and at least one of age, year, isolate collection date, isolate sequencing date, and variation in a sequence measured by multilocous sequence typing;

supplying the data set of the plurality of features and the set of labels to a processor configured to execute instructions stored on a memory to provide a variance analysis engine, wherein the variance analysis engine is configured to generate an effect size for each of the labels on the data set of the plurality of features;

supplying as output from the variance analysis engine to a sizing module at least one effect size generated for a label;

selecting, via the sizing module, at least one label to be used in a machine learning model based on the at least one supplied effect size; and training, using the selected at least one label with a data set, a machine learning model to predict antibiotic drug susceptibility.

2. The method of claim 1, wherein the data set of the plurality of features is a genomic dataset including at least one of a gene presence-absence matrix, an SNP matrix, a plasmid profiling matrix, a mobile genetic matrix, a gene expression matrix, an RNA sequence matrix, and a microarray matrix.

3. The method of claim 1, wherein the set of labels is a single vector of binary values.

4. The method of claim 1, wherein the set of labels is a single vector of multi-class values.

5. The method of claim 1, wherein selecting the at least one label via the sizing module includes selecting the at least one label based on its generated effect size exceeding a predetermined threshold.

6. The method of claim 1, further comprising ranking, via the sizing module, the plurality of labels based on their effect size and selecting, via the sizing module, the at least one label based on the ranking.

7. The method of claim 1, wherein the data set of a plurality of features is a feature matrix including a plurality of genomic features and a plurality of isolates, and wherein the covariate matrix includes the plurality of phenotypes and the plurality of isolates.

8. A system for training a model for predicting antibiotic drug susceptibility, the system comprising:

an interface for receiving a data set of a plurality of features and a set of labels that are related to the plurality of features; wherein the set of labels is a covariate matrix including a plurality of phenotypes, and the plurality of phenotypes includes susceptibilities to various antibiotics and at least one of age, year, isolate collection date, isolate sequencing date, and variation in a sequence measured by multilocous sequence typing;

a memory; and a processor configured to execute instructions stored on the memory to: (i) provide a variance analysis engine configured to receive the data set of the plurality of features and the set of labels; (ii) output an effect size for each of the labels, wherein at least one label is selected to be used in a machine learning model based on its effect size; and (iii) train, using the selected at least one label with a data set, a machine learning model to predict antibiotic drug susceptibility.

9. The system of claim 8, wherein the data set of the plurality of features is a genomic dataset including at least one of a gene presence-absence matrix, an SNP matrix, a plasmid profiling matrix, a mobile genetic element matrix, a gene expression matrix, an RNA sequence matrix, and a microarray matrix.

10. The system of claim 8, wherein the set of labels is a single vector of binary values.

11. The system of claim 8, wherein the set of labels is a single vector of multi-class values.

12. The system of claim 8, wherein the at least one selected label is selected based on its generated effect size exceeding a predetermined threshold.

13. The system of claim 8, wherein the variance analysis engine is further configured to rank the set of labels based on their effect size and select the at least one label based on the ranking.

14. The system of claim 8, wherein the data set of a plurality of features is a feature matrix including a plurality of genomic features and a plurality of isolates, and wherein the covariate matrix includes the plurality of phenotypes and the plurality of isolates.

* * * * *